(12) United States Patent
Kim et al.

(10) Patent No.: US 12,070,536 B2
(45) Date of Patent: Aug. 27, 2024

(54) DEODORIZATION AND DEHUMIDIFICATION DEVICE

(71) Applicant: Samsung Electronics Co., Ltd., Suwon-si (KR)

(72) Inventors: Minsoo Kim, Suwon-si (KR); Heemoon Jeong, Suwon-si (KR); Jinyounggeul Oh, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 463 days.

(21) Appl. No.: 17/060,044

(22) Filed: Sep. 30, 2020

(65) Prior Publication Data

US 2021/0093743 A1    Apr. 1, 2021

(30) Foreign Application Priority Data

Sep. 30, 2019   (KR) .................. 10-2019-0120952

(51) Int. Cl.
*A61L 9/00* (2006.01)
*A61L 2/00* (2006.01)
*A61L 9/18* (2006.01)
*B01D 53/00* (2006.01)
*B01D 53/04* (2006.01)
(Continued)

(52) U.S. Cl.
CPC ............. *A61L 9/18* (2013.01); *B01D 53/007* (2013.01); *B01D 53/0446* (2013.01); *B01D 53/265* (2013.01); *B01D 53/885* (2013.01); *A61L 2209/13* (2013.01); *A61L 2209/14* (2013.01); *B01D 2253/102* (2013.01); *B01D 2255/802* (2013.01); *B01D 2257/80* (2013.01); *B01D 2257/90* (2013.01)

(58) Field of Classification Search
CPC .......................... A61L 9/205; B01D 53/0446
See application file for complete search history.

(56) References Cited

U.S. PATENT DOCUMENTS

| | | | | |
|---|---|---|---|---|
| 5,369,892 | A * | 12/1994 | Dhaemers | F26B 21/00 34/224 |
| 8,484,861 | B2 * | 7/2013 | Park | D06F 73/02 219/400 |
| 11,015,284 | B2 * | 5/2021 | Cacho | F26B 21/006 |

(Continued)

FOREIGN PATENT DOCUMENTS

| | | |
|---|---|---|
| EP | 1472968 A1 | 11/2004 |
| JP | 3418529 B2 | 6/2003 |

(Continued)

OTHER PUBLICATIONS

Office Action issued May 27, 2024, in connection with Korean Patent Application No. 10-2019-0120952, 21 pages.

*Primary Examiner* — Kevin Joyner

(57) ABSTRACT

A deodorization and dehumidification device including an accommodation room in which an object is accommodated, a deodorizer including a deodorization route provided outside the accommodation room to deodorize air in the accommodation room and supply the deodorized air to the accommodation room, and a dehumidifier including a dehumidification route provided outside the accommodation room and separated from the deodorization route to dehumidify air in the accommodation room and supply the dehumidified air to the accommodation room.

8 Claims, 14 Drawing Sheets

(51) Int. Cl.
*B01D 53/26* (2006.01)
*B01D 53/88* (2006.01)

(56) References Cited

U.S. PATENT DOCUMENTS

| | | | |
|---|---|---|---|
| 2013/0224085 A1* | 8/2013 | Antinozzi | A61L 2/202 |
| | | | 422/186.08 |
| 2014/0105783 A1* | 4/2014 | Levsen | A47L 23/205 |
| | | | 422/186.05 |

FOREIGN PATENT DOCUMENTS

| | | |
|---|---|---|
| JP | 3535135 B2 | 6/2004 |
| JP | 2007-236749 A | 9/2007 |
| KR | 20-0347100 Y1 | 4/2004 |
| KR | 10-2006-0016821 A | 2/2006 |
| KR | 10-2014-0063035 A | 5/2014 |
| KR | 10-2015-0131690 A | 11/2015 |
| KR | 10-1703148 B1 | 2/2017 |
| KR | 10-1938420 B1 | 4/2019 |

* cited by examiner

DEODORIZATION AND DEHUMIDIFICATION DEVICE

CROSS-REFERENCE TO RELATED APPLICATION

This application is based on and claims priority under 35 U.S.C. § 119 to Korean Patent Application No. 10-2019-0120952 filed on Sep. 30, 2019 in the Korean Intellectual Property Office, the disclosure of which is incorporated by reference herein in its entirety.

BACKGROUND

1. Field

The disclosure relates to a deodorization and dehumidification device, and more particularly, to a deodorization and dehumidification device capable of efficiently sterilizing, deodorizing, and dehumidifying an object.

2. Description of the Related Art

A conventional deodorization and dehumidification device uses a method of discharging air to the outside after performing deodorization and dehumidification of a specific space.

Generally, a conventional deodorization and dehumidification device includes an accommodation room having an accommodating portion forming a space that is open to the front to accommodate shoes, an inlet provided on one side of the accommodating portion to suck air, a dehumidifying and deodorizing portion for dehumidifying and deodorizing the air sucked through the inlet, and an outlet provided on the other side of the accommodating portion to discharge the dehumidified and deodorized air.

However, in the conventional deodorization and dehumidification device, in a process in which air dehumidified and deodorized by the dehumidifying and deodorizing portion is discharged to the outside through the outlet, odors in the accommodating portion may be discharged to the outside together with the air.

SUMMARY

It is an aspect of the disclosure to provide a deodorization and dehumidification device capable of preventing odors from being discharged to the outside of the device.

It is another aspect of the disclosure to provide a deodorization and dehumidification device capable of improving deodorization and dehumidification efficiencies by performing deodorization and dehumidification of an object through routes different from each other.

Additional aspects of the disclosure will be set forth in part in the description which follows and, in part, will be obvious from the description, or may be learned by practice of the disclosure.

In accordance with an aspect of the disclosure, a deodorization and dehumidification device includes an accommodation room in which an object is accommodated, a deodorizer including a deodorization route provided outside the accommodation room to deodorize air in the accommodation room and supply the deodorized air to the accommodation room, and a dehumidifier including a dehumidification route provided outside the accommodation room and separated from the deodorization route to dehumidify air in the accommodation room and supply the dehumidified air to the accommodation room.

The deodorizer may include a first inlet communicating with the accommodation room to allow air in the accommodation room to be introduced, and a first outlet communicating with the accommodation room to allow the deodorized air to be supplied to the accommodation room.

The deodorizer may further include a first fan configured to suck air in the accommodation room through the first inlet, and a filter member configured to remove odor particles contained in the sucked air.

The filter member may include at least one of an activated carbon filter configured to adsorb and remove the odor particles by including activated carbon and a photocatalytic filter configured to decompose and remove the odor particles by irradiating light to the odor particles.

The deodorizer may further include a heater configured to remove moisture contained in the air passed through the filter member by supplying heat.

The dehumidifier may include a second inlet communicating with the accommodation room to allow air in the accommodation room to be introduced, and a second outlet communicating with the accommodation room to allow dehumidified air to be supplied to the accommodation room.

The dehumidifier may further include a second fan configured to suck air in the accommodation room into the inside thereof, and a filtering member configured to filter out foreign matter contained in the sucked air.

The deodorization and dehumidification device may further include a heat pump including a compressor, a condenser, an expansion valve, and an evaporator to dehumidify the air sucked into the inside.

The deodorization and dehumidification device may further include a thermoelectric module including a heat absorbing plate and a heat radiating plate to dehumidify the air sucked into the inside.

The deodorization and dehumidification device may further include a flow pipe connected to the first outlet and extending in one direction inside the accommodation room to guide the movement of the deodorized air, and at least one holder connected to the flow pipe and on which the object is mounted so that the deodorized air is supplied to the object.

A plurality of the holder arranged to be spaced apart a predetermined distance in an extending direction of the flow pipe may be provided, and guide members arranged to increase in height toward a direction in which the deodorized air moves along the flow pipe may be provided at a bottom portion of the flow pipe where the holders are located.

In accordance with another aspect of the disclosure, a deodorization and dehumidification device includes an accommodation room in which an object is accommodated, a deodorizer including a first fan configured to suck air in the accommodation room and performing a deodorization mode in which the sucked air is deodorized and then the deodorized air is supplied to the accommodation room, a dehumidifier including a second fan configured to suck air in the accommodation room and performing a dehumidification mode in which the sucked air is dehumidified and then the dehumidified air is supplied to the accommodation room, and a controller configured to selectively drive the first fan and the second fan to selectively perform the deodorization mode and the dehumidification mode.

In accordance with another aspect of the disclosure, a deodorization and dehumidification device includes an accommodation room in which an object is accommodated, a deodorizer including a first inlet communicating with the accommodation room to allow air in the accommodation room to be introduced and performing deodorization of the air introduced through the first inlet, a dehumidifier including a second inlet communicating with the accommodation room to allow air in the accommodation room to be introduced and performing dehumidification of the air introduced through the second inlet, and a mixing guide member including an outlet communicating with the accommodation room and configured to guide the air supplied from each of the deodorizer and the dehumidifier to be supplied to the accommodation room through the outlet and mixed in the accommodation room.

The deodorizer may include a first pipe extending from the first inlet, and a first outlet communicating with the mixing guide member to allow air passed through the first pipe to be supplied to the mixing guide member, and the dehumidifier may include a second pipe extending from the second inlet, and a second outlet communicating with the mixing guide member to allow air passed through the second pipe to be supplied to the mixing guide member.

The deodorization and dehumidification device may further include a flow pipe connected to the mixing guide member and extending in one direction inside the accommodation room so that the air supplied from the mixing guide member moves in the one direction and is mixed, and at least one holder provided on the flow pipe and holding the object so that the mixed air is supplied to the object.

In accordance with another aspect of the disclosure, a deodorization and dehumidification device includes an accommodation room including, a holder on which an object is mounted, a deodorizer provided outside the accommodation room and configured to deodorize air in the accommodation room and supply the deodorized air to the inside of the holder to deodorize the inside of the object, and a dehumidifier provided outside the accommodation room and configured to dehumidify air in the accommodation room and supply the dehumidified air to the inside or outside of the holder to dehumidify the object.

The deodorizer may include a first inlet communicating with the accommodation room to allow air in the accommodation room to be introduced, and a first outlet communicating with the accommodation room to allow the deodorized air to be supplied to the accommodation room.

A flow pipe connected to the first outlet and extending in an extension direction of the accommodation room to allow the deodorized air to move in the extension direction of the accommodation room may be provided inside the accommodation room, and the holder may be provided on the flow pipe.

The holder may have a hollow shape with an upper end portion and an open lower end portion open, and allow the air moving along the flow pipe to pass through the lower end portion and be supplied to the inside of the object through the upper end portion.

The dehumidifier may include a second inlet communicating with the accommodation room to allow air in the accommodation room to be introduced, and a second outlet communicating with the accommodation room to allow the dehumidified air to be supplied to the accommodation room, and spaced apart from the holder by a predetermined distance.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

FIGS. 1A through 12, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system or device.

Configurations shown in the embodiments and the drawings described in the present specification are only the preferred embodiments of the present disclosure, and thus it is to be understood that various modified examples, which may replace the embodiments and the drawings described in the present specification, are possible when filing the present application.

Like reference numbers or signs in the various figures of the application represent parts or components that perform substantially the same functions.

The terms used herein are for the purpose of describing the embodiments and are not intended to restrict and/or to limit the disclosure. For example, the singular expressions herein may include plural expressions, unless the context clearly dictates otherwise. Also, the terms "comprises" and "has" are intended to indicate that there are features, numbers, steps, operations, elements, parts, or combinations thereof described in the specification, and do not exclude the presence or addition of one or more other features, numbers, steps, operations, elements, parts, or combinations thereof.

It will be understood that although the terms first, second, etc. may be used herein to describe various components, these components should not be limited by these terms, and the terms are only used to distinguish one component from another. For example, without departing from the scope of the disclosure, the first component may be referred to as a second component, and similarly, the second component may also be referred to as a first component. The term "and/or" includes any combination of a plurality of related items or any one of a plurality of related items.

Hereinafter, embodiments of the disclosure will be described in detail with reference to the accompanying drawings.

Figure 1A:
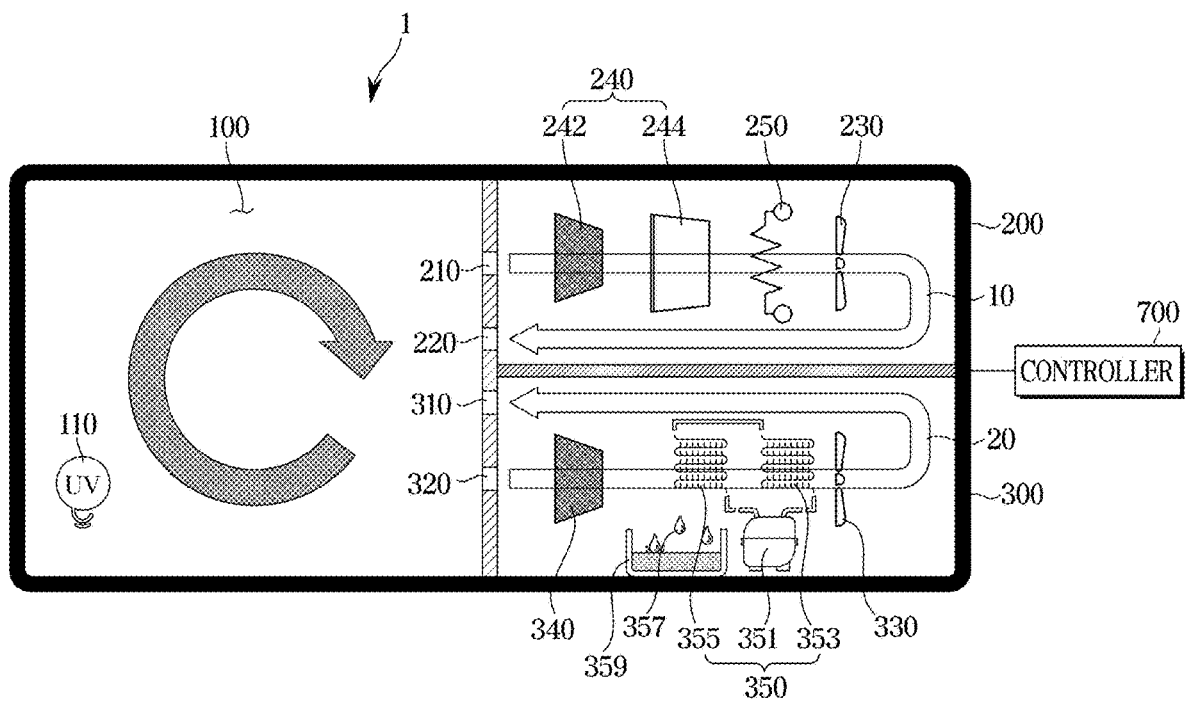
FIG. 1A illustrates a schematic view of a deodorization and dehumidification device according to an embodiment of the disclosure.
Figure 1B:
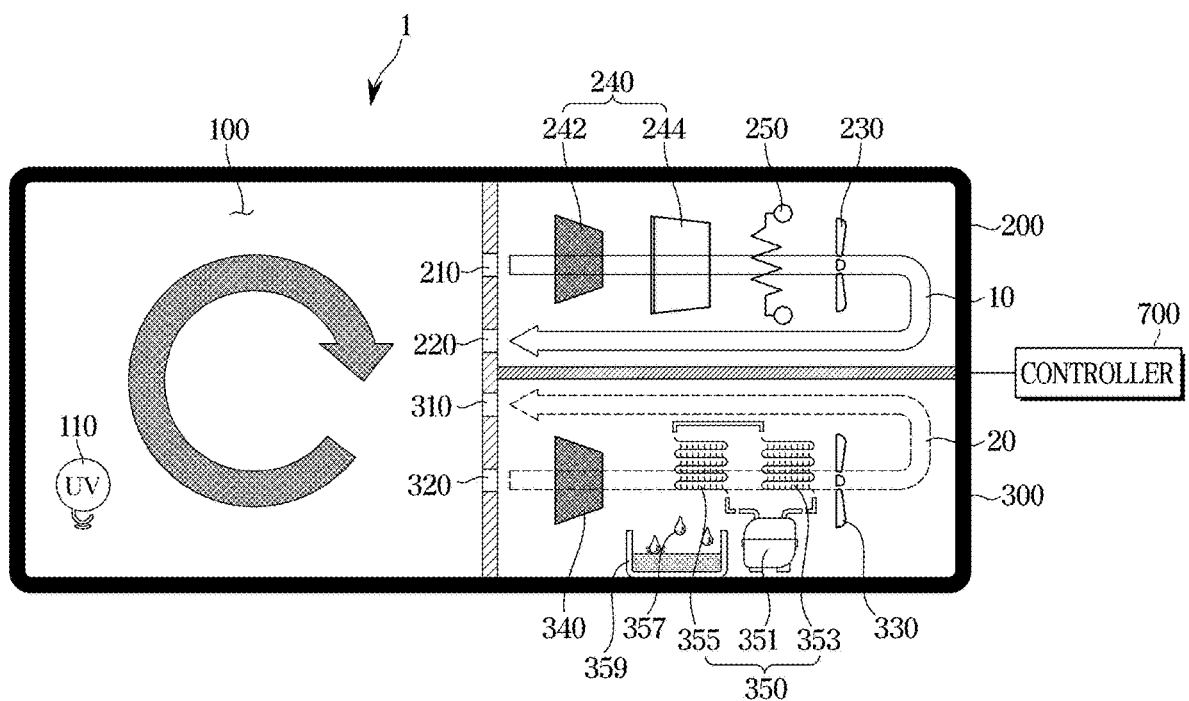
FIG. 1B illustrates that the deodorization and dehumidification device in FIG. 1A operates in a deodorization mode.
Figure 1C:
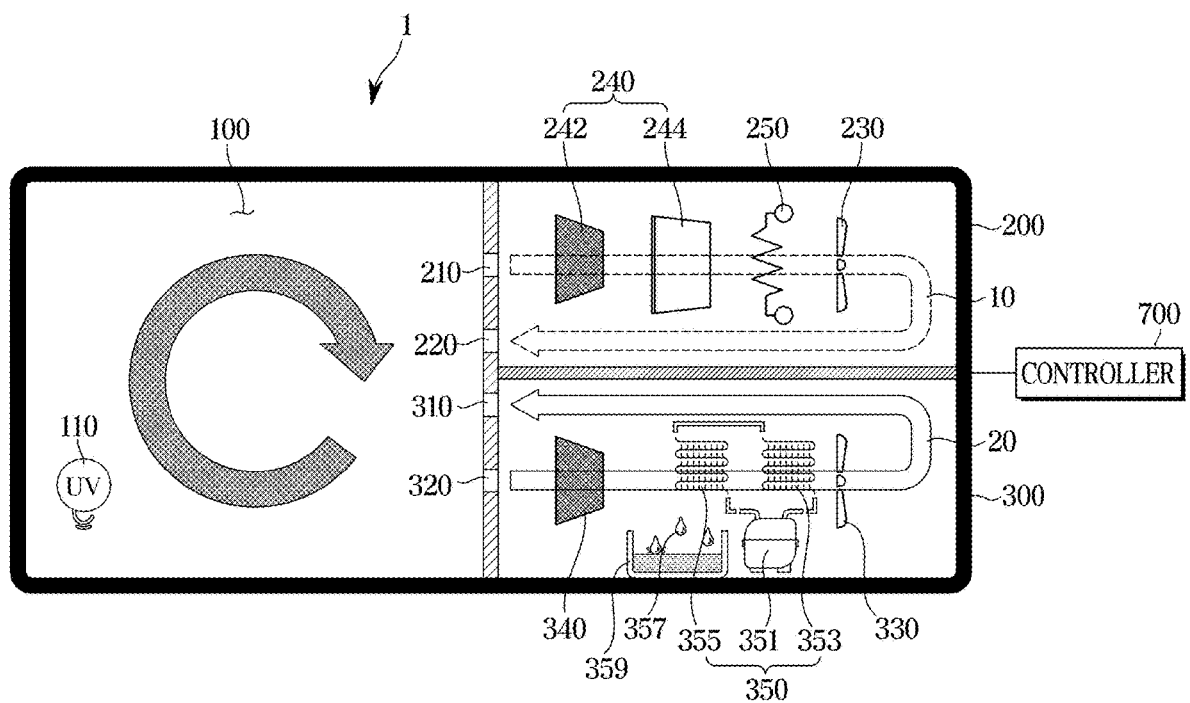
FIG. 1C illustrates that the deodorization and dehumidification device in FIG. 1A operates in a dehumidification mode.

FIG. 1A is a schematic view of a deodorization and dehumidification device according to an embodiment of the disclosure, FIG. 1B illustrates that the deodorization and dehumidification device in FIG. 1A operates in a deodorization mode, and FIG. 1C illustrates that the deodorization and dehumidification device in FIG. 1A operates in a dehumidification mode.

Referring to FIG. 1A, a deodorization and dehumidification device 1 according to an embodiment of the disclosure includes an accommodation room 100, a deodorizer 200, and a dehumidifier 300.

The accommodation room 100 is provided with an accommodation space in which an object is accommodated. The accommodation room 100 is formed such that at least one side thereof is open so that an object may be accommodated therein. An ultraviolet irradiator 110 is installed inside the accommodation room 100 to sterilize an object by irradiating ultraviolet rays to the object. For example, the ultraviolet irradiator 110 may be composed of various light emitting devices that irradiate ultraviolet rays, such as a UV lamp and an LED. The drawings illustrate that one of the ultraviolet irradiator 110 is provided, but two or more of the ultraviolet irradiators 110 may be additionally installed within the accommodation room 100.

The deodorizer 200 and the dehumidifier 300 are provided outside the accommodation room 100 to perform deodorization and dehumidification of an object located inside the accommodation room 100, respectively.

When air in the accommodation room 100 is introduced, the deodorizer 200 deodorizes the air and then supplies the deodorized air back to the accommodation room 100 so that the object in the accommodation room 100 is deodorized. When air in the accommodation room 100 is introduced, the dehumidifier 300 dehumidifies the air and then supplies the dehumidified air back to the accommodation room 100 so that the object in the accommodation room 100 is dehumidified.

That is, as indicated by arrows in FIG. 1A, one part of air in the accommodation room 100 is continuously circulated in a manner of being supplied back to the accommodation room 100 after being deodorized in the deodorizer 200, and the other part of air in the accommodation room 100 is continuously circulated in a manner of being supplied back to the accommodation room 100 after being dehumidified in the dehumidifier 300.

In other words, air in the accommodation room 100 is circulated along a deodorization route 10 inside the deodorizer 200 and a dehumidification route 20 inside the dehumidifier 300, so that deodorization and dehumidification may be simultaneously performed. In this case, one part of air in the accommodation room 100 is deodorized while moving along the deodorization route 10, and the other part of air in the accommodation room 100 is dehumidified while moving along the dehumidification route 20 separated from the deodorization route 10.

More specifically, the deodorizer 200 includes a first inlet 210 communicating with the accommodation room 100 to allow air in the accommodation room 100 to be introduced, and a first outlet 220 communicating with the accommodation room 100 to allow the deodorized air to be supplied back to the accommodation room 100.

Accordingly, the air introduced into the deodorizer 200 through the first inlet 210 is deodorized and then supplied to the accommodation room 100 through the first outlet 220.

The deodorizer 200 may further include a first fan 230, a filter member 240, and a heater 250.

The first fan 230 is positioned inside the deodorizer 200 and includes a plurality of blades. When the first fan 230 rotates, air in the accommodation room 100 is introduced into the deodorizer 200 through the first inlet 210.

The filter member 240 filters air introduced into the deodorizer 200. Air in the accommodation room 100 is moved to the inside of the deodorizer 200 together with odor particles contained in an object located inside the accommodation room 100, and in this case, the filter member 240 may remove the odor particles contained in the air.

For example, the filter member 240 may be a filter including at least one of an activated carbon filter 242 to adsorb and remove odor particles by including activated carbon and a photocatalytic filter 244 to decompose and remove odor particles by irradiating light to the odor particles. Also, the filter member 240 may be a filter that decomposes and removes odor particles using plasma or negative ions.

The heater 250 may provide heat to remove moisture contained in air passed through the filter member 240. That is, the heater 250 may additionally perform dehumidification of air even in the deodorizer 200 by applying heat to the air from which odor particles have been removed.

FIG. 1A illustrates that the filter member 240, the heater 250, and the first fan 230 are sequentially positioned along the inflow direction of air, but the filter member 240, the heater 250, and the first fan 230 may be changed in position. Also, it is illustrated that one of the first fan 230 is provided inside the deodorizer 200, but a plurality of the first fans 230 may be provided on the deodorization route 10 for smooth circulation of air.

The dehumidifier 300 includes a second inlet 310 communicating with the accommodation room 100 to allow air in the accommodation room 100 to be introduced, and a second outlet 320 communicating with the accommodation room 100 to allow the dehumidified air to be supplied to the accommodation room 100.

Accordingly, the air introduced into the dehumidifier 300 through the second inlet 310 may be dehumidified and then supplied to the accommodation room 100 through the second outlet 320.

The dehumidifier 300 may further include a second fan 330, a filtering member 340, and a heat pump 350.

The second fan 330 includes a plurality of blades and introduces air in the accommodation room 100 into the dehumidifier 300 through rotation.

The filtering member 340 filters the air introduced into the dehumidifier 300 by the second fan 330.

When foreign matter contained in the air is filtered out by the filtering member 340, the heat pump 350 dehumidifies the filtered air. The heat pump 350 includes an evaporator 355 evaporating a refrigerant and converting the evaporated refrigerant into a low temperature and low pressure refrigerant, a compressor 351 compressing the refrigerant, a condenser 353 condensing a high temperature and high pressure refrigerant compressed by the compressor 351, and an expansion device (not shown) expanding the refrigerant condensed by the condenser 353. The compressor 351, the condenser 353, the expansion valve, and the evaporator 355 are connected through a connection pipe to perform heat exchange between the refrigerant and air.

The humid air that has absorbed moisture from an object in the accommodation room 100 is dehumidified while exchanging heat with the refrigerant in a low temperature and low pressure state in the evaporator 355, and moisture in the air is discharged as condensate water 357. The discharged condensate water 357 is stored in a storage tank 359.

After that, the air from which the condensate water 357 is discharged is heated by heat exchange with the refrigerant in a high temperature and high pressure state in the condenser 353 and supplied into the accommodation room 100. Air may continuously circulate through the accommodation room 100 and the dehumidifier 300 through this process to remove moisture in the object.

Likewise, FIG. 1A illustrates that the filtering member 340, the heat pump 350, and the second fan 330 are sequentially positioned along the inflow direction of air, but the filtering member 340, the heat pump 350, and the second fan 330 may be changed in position. Also, it is illustrated that one of the second fan 330 is provided inside the dehumidifier 300, but a plurality of the second fans 330 may be provided on the dehumidification route 20 for smooth circulation of air.

As described above, the deodorization and dehumidification device 1 may simultaneously perform the deodorization mode and the dehumidification mode in the deodorizer 200 and the dehumidifier 300. Alternatively, the deodorization and dehumidification device 1 may selectively perform the deodorization mode performed in the deodorizer 200 and the dehumidification mode performed in the dehumidifier 300.

That is, when the deodorization and dehumidification device 1 drives the first fan 230, as illustrated in FIG. 1B, air in the accommodation room 100 may be introduced into the deodorizer 200, and thus a deodorization operation for the introduced air may be performed.

On the other hand, when the deodorization and dehumidification device 1 drives the second fan 330, as illustrated in FIG. 1C, air in the accommodation room 100 may be introduced into the dehumidifier 300, and thus a dehumidification operation for the introduced air may be performed.

A controller 700 may be provided to selectively drive the first fan 230 and the second fan 330. That is, the controller 700 may perform deodorization or dehumidification of air or both deodorization and dehumidification of air by selectively or both driving the first fan 230 and the second fan 330.

Figure 2:
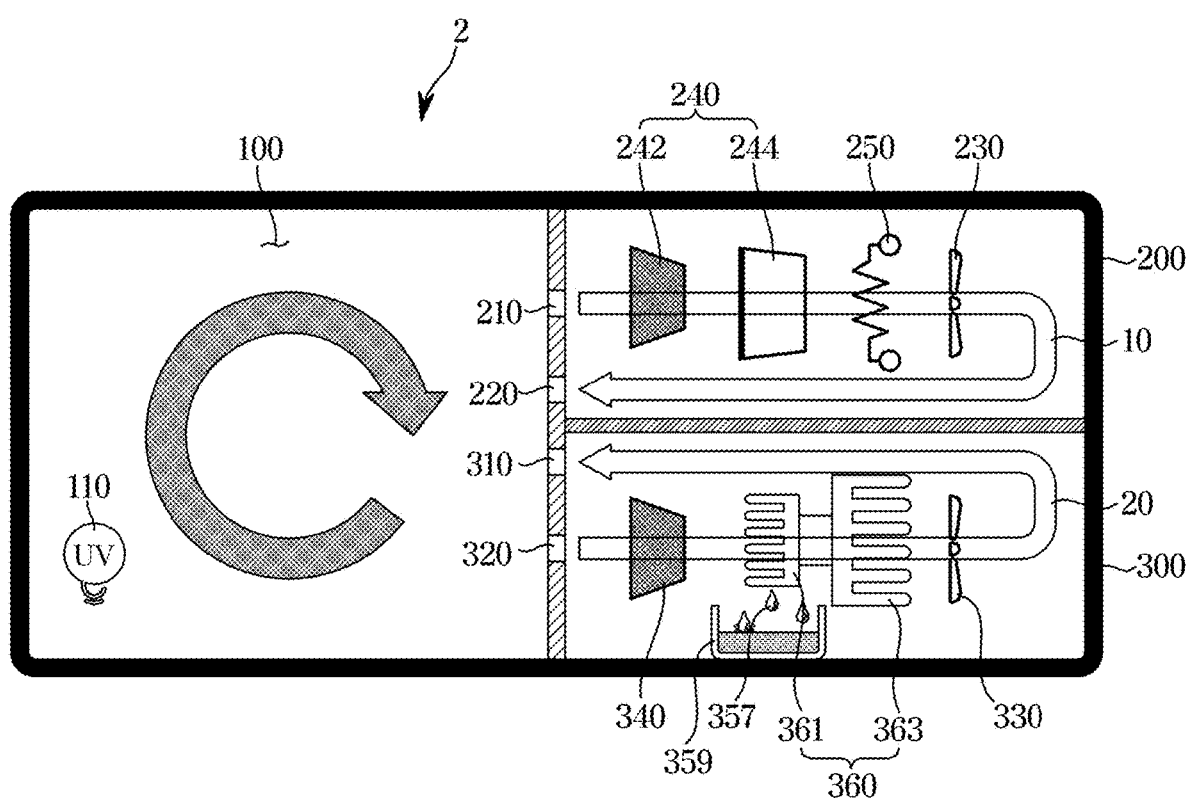
FIG. 2 illustrates a schematic view of a deodorization and dehumidification device according to another embodiment of the disclosure.

FIG. 2 is a schematic view of a deodorization and dehumidification device according to another embodiment of the disclosure.

A deodorization and dehumidification device 2 illustrated in FIG. 2 is the same as the deodorization and dehumidification device 1 described with reference to FIGS. 1A to 1C, except that the dehumidifier 300 includes a thermoelectric module 360 instead of the heat pump 350, and thus description of the same components will be omitted.

In the deodorization and dehumidification device 2 in FIG. 2, the dehumidifier 300 includes the thermoelectric module 360 provided for dehumidifying air. The thermoelectric module 360 includes a heat absorbing plate 361 and a heat radiating plate 363 to dehumidify air introduced into the dehumidifier 300.

The air introduced into the dehumidifier 300 passes through the heat absorbing plate 361 in a humid state by absorbing moisture from an object in the accommodation room 100, and the moisture in the air is discharged as the condensate water 357. After that, the air passes through the heat radiating plate 363 to be supplied into the accommodation room in a state of a high temperature and then absorbs moisture in the object again. Air may remove moisture from the object by repeating this process.

Figure 3:
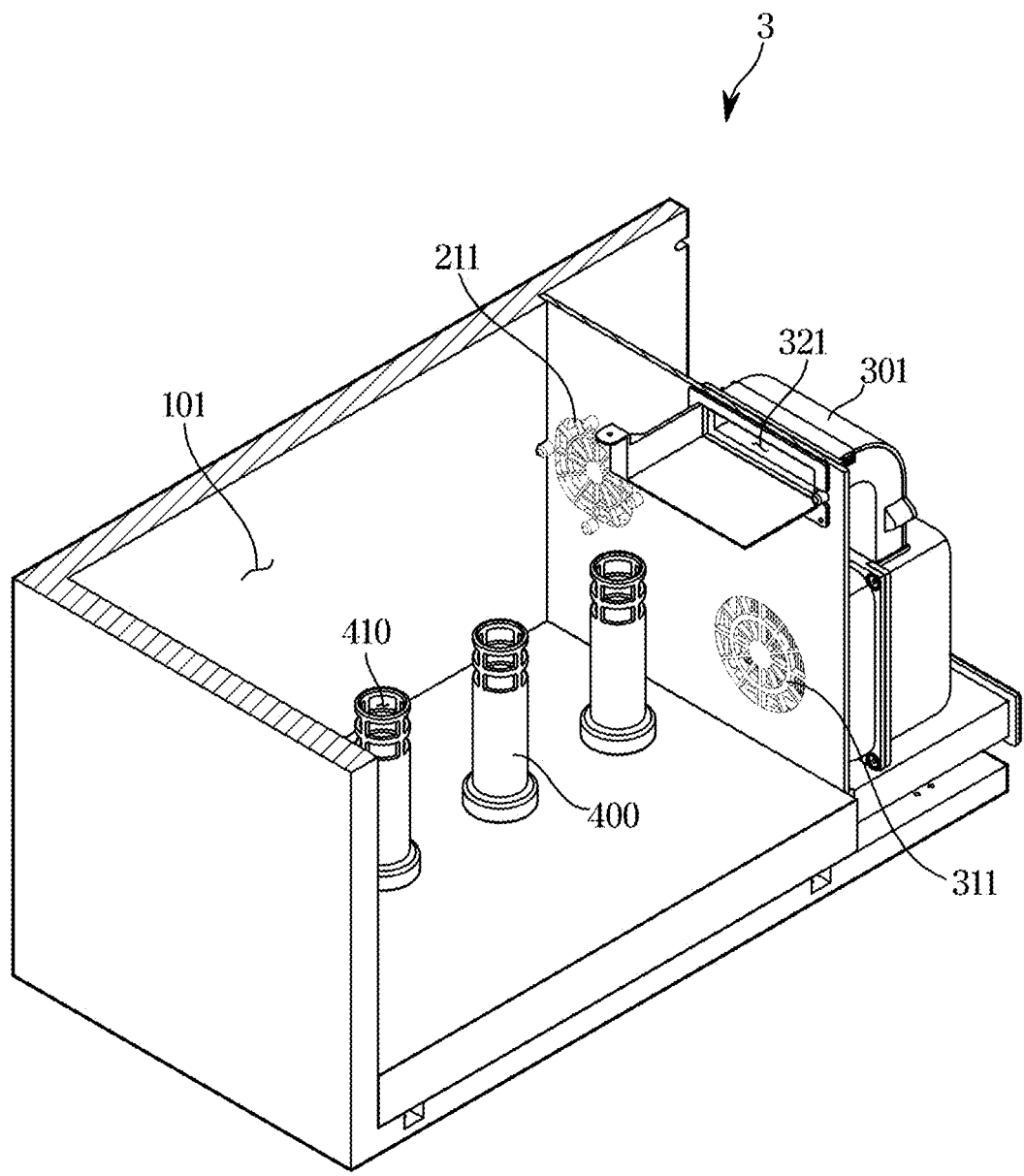
FIG. 3 illustrates a perspective view of a deodorization and dehumidification device according to another embodiment of the disclosure.
Figure 4:
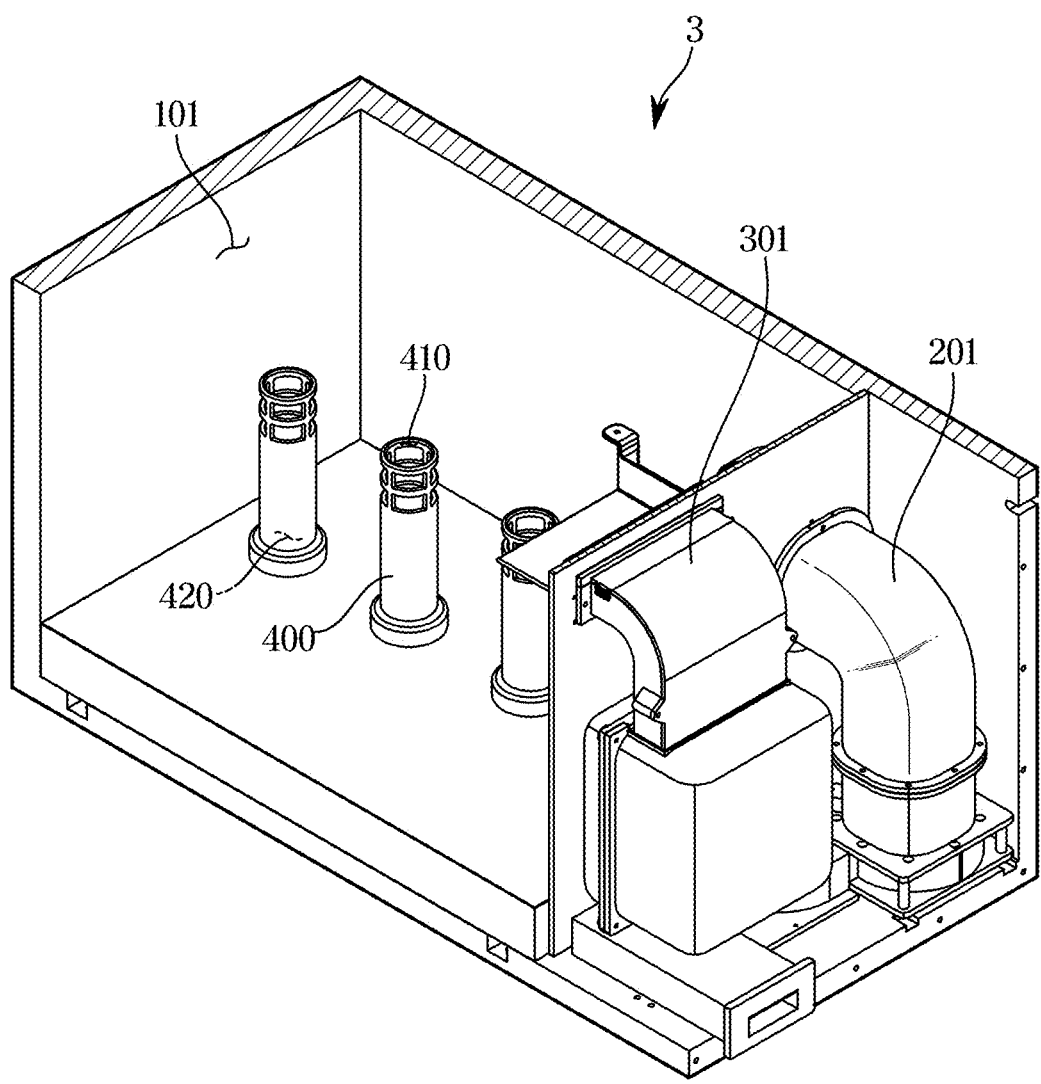
FIG. 4 illustrates a perspective view of the deodorization and dehumidification device in FIG. 3, viewed from a different angle.
Figure 5:
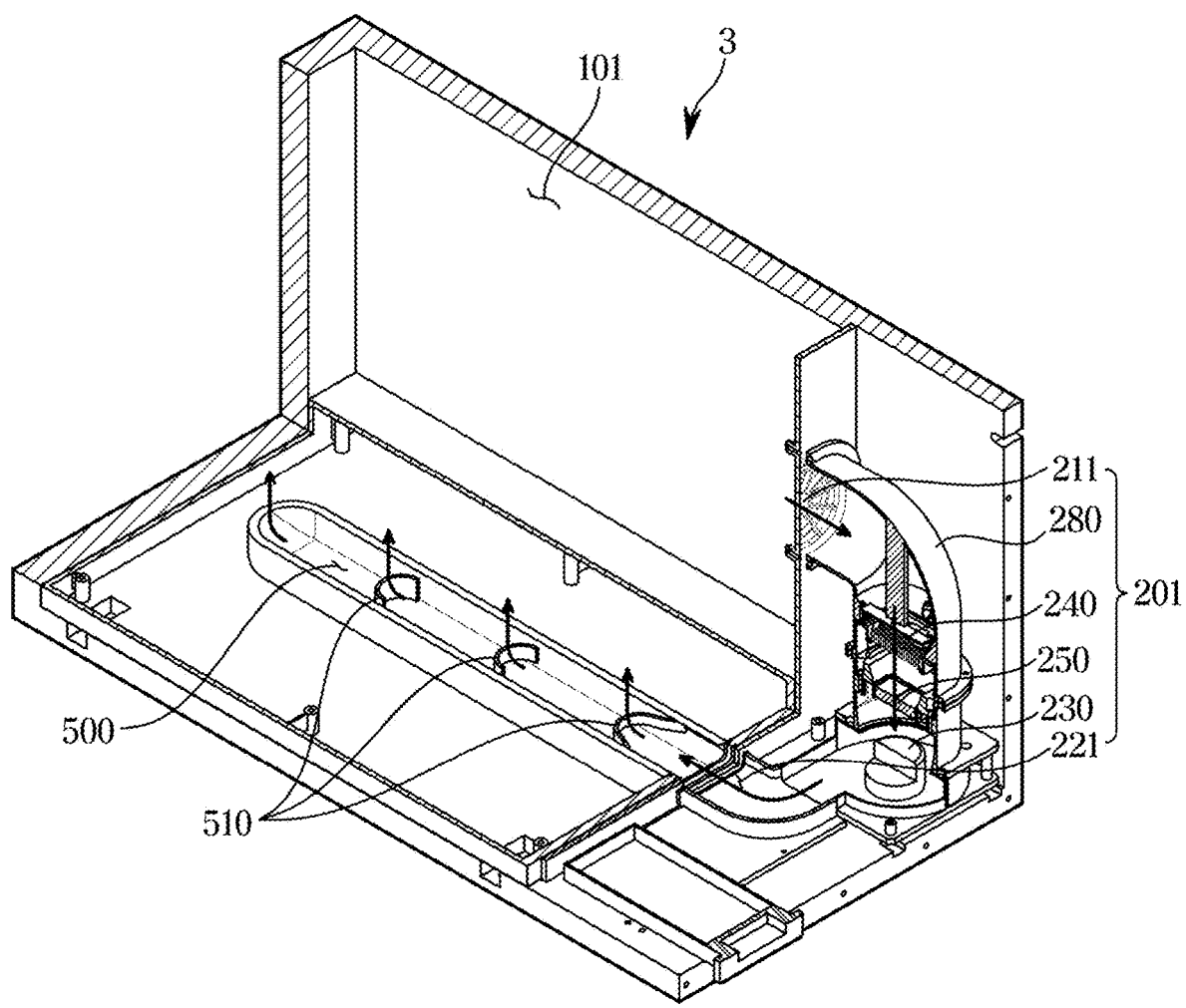
FIG. 5 illustrates a deodorization route in the deodorization and dehumidification device in FIG. 3.
Figure 6:
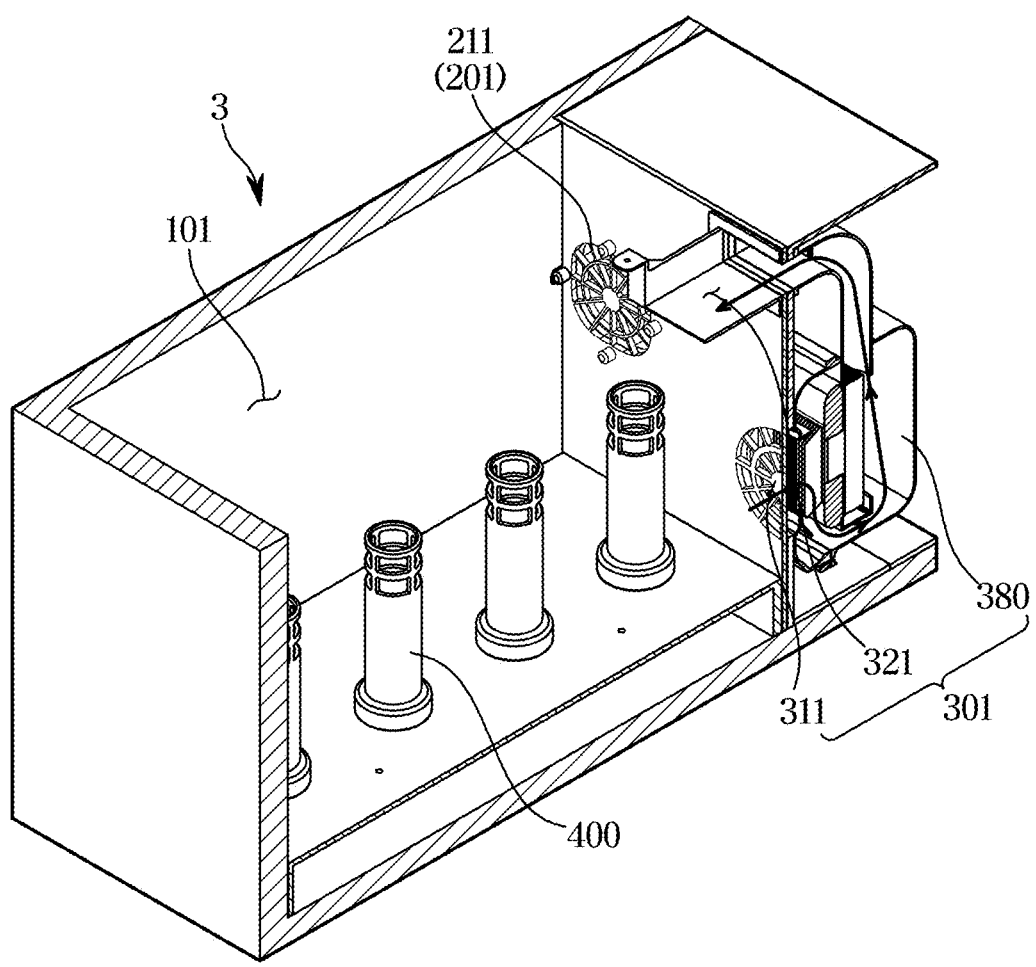
FIG. 6 illustrates a dehumidification route in the deodorization and dehumidification device in FIG. 3.

FIG. 3 is a perspective view of a deodorization and dehumidification device according to another embodiment of the disclosure, FIG. 4 is a perspective view of the deodorization and dehumidification device in FIG. 3, viewed from a different angle, FIG. 5 illustrates a deodorization route in the deodorization and dehumidification device in FIG. 3, and FIG. 6 illustrates a dehumidification route in the deodorization and dehumidification device in FIG. 3.

Referring to FIGS. 3 and 4, a deodorization and dehumidification device 3 includes an accommodation room 101, a deodorizer 201 and a dehumidifier 301.

The accommodation room 101 is formed as a closed space in which one side may be opened and closed, but the drawings illustrate that front and upper covers are excluded.

A holder 400 is provided inside the accommodation room 101 so that an object is mounted on the holder 400 to be deodorized and dehumidified.

For example, the object may be a shoe. In this case, the accommodation room 101 may be provided in a shape having an appropriate space in consideration of the characteristics of the shoe, and the holder 400 may be provided in a shape capable of mounting shoes according to the type and size of each shoe.

The deodorizer 201 and the dehumidifier 301 are provided outside the accommodation room 101. The drawing illustrates that the deodorizer 201 and the dehumidifier 301 are positioned side by side, but the positions of the deodorizer 201 and the dehumidifier 301 are not limited thereto, and the deodorizer 201 and the dehumidifier 301 may be disposed to be spaced apart from each other as long as they are provided outside the accommodation room 101.

Referring to FIG. 5, the deodorizer 201 includes a first inlet 211, a first pipe 280 and a first outlet 221.

The first inlet 211 communicates with the accommodation room 101 to allow air in the accommodation room 101 to be introduced into the deodorizer 201.

The first pipe 280 extends downward from the first inlet 211, and the first fan 230, the filter member 240, and the heater 250 may be provided in the first pipe 280. Because the first fan 230, the filter member 240, and the heater 250 have been described above, a description thereof will be omitted.

Accordingly, air in the accommodation room 101 is introduced into the deodorizer 201 by a suction power of the first fan 230, the introduced air moves downward along the first pipe 280 of the deodorizer 201, and odor particles contained in the air are removed by the filter member 240 to be deodorized.

The deodorized air is supplied back to the accommodation room 101 through the first outlet 221.

A flow pipe 500 connected to the first outlet 221 and extending along an extending direction of the accommodation room 101 is formed at a bottom portion of the accommodation room 101, and the holder 400 is provided on the flow pipe 500 to communicate with the flow pipe 500. Thus, the deodorized air passed through the first outlet 221 moves along the extension direction of the accommodation room 101 and may be supplied into the holder 400.

In this case, referring to FIG. 3, the holder 400 may be formed in a hollow shape in which an upper end portion 410 and a lower end portion 420 (refer to FIG. 4) are opened. Accordingly, the air moved along the flow pipe 500 and introduced into the lower end 420 of the holder 400 may move to the upper end portion 410 of the holder 400 and be supplied to the object mounted on the holder 400.

The object may be mounted on the holder 400 such that the inside of the object faces the upper end portion 410 of the holder 400, and thus, the air passed through the upper end portion 410 of the holder 400 moves to the inside of the object, so that the inside of an object may be deodorized. That is, when the object is a shoe, the shoe has an opening in a portion surrounding an ankle of a wearer and thus may be mounted on the holder 400 so that the opening faces the upper end portion 410 of the holder 400. Alternatively, the upper end portion 410 of the holder 400 may be inserted into the shoe. As a result, the air passed through the holder 400 is deeply introduced into the shoe through the opening to efficiently perform deodorization of the shoe, so that the wearer may use the shoe in a comfortable state.

A plurality of the holders 400 is provided such that the object is mounted on each of the holders 400, so that deodorization and dehumidification of a plurality of the objects may be simultaneously performed. In this case, the holders 400 may be disposed to be spaced a predetermined distance along the extending direction of the flow pipe 500 as illustrated in the drawing.

At a bottom portion of the flow pipe 500 where the holders 400 are located, U-shaped guide members 510 arranged to increase in height toward a direction in which the deodorized air moves along the flow pipe 500 may be provided. That is, the guide members 510 are provided at a portion where the flow pipes 500 and the holder 400 communicate and may be arranged to increase in height along the direction of air moving along the flow pipe 500 from the first outlet 221.

The air passed through the first outlet 221 moves along the flow pipe 500 and is introduced into the holders 400 by changing a traveling direction thereof by the guide members 510. In this case, the air passed through the first outlet 221 may continuously move along the flow pipe 500 by first encountering the guide members 510 having a relatively low height, so that the air may be evenly introduced into each of the holders 400. Accordingly, the object mounted on each of the holders 400 may be efficiently deodorized and dehumidified.

Referring to FIGS. 3 and 6, the dehumidifier 301 includes a second inlet 311, a second pipe 380, and a second outlet 321.

The second inlet 311 communicates with the accommodation room 101 to allow air in the accommodation room 101 to be introduced into the dehumidifier 301, and the second outlet 321 communicates with the accommodation room 101 to allow dehumidified air to be supplied back to the accommodation room 101. The second inlet 311 and the second outlet 321 may be formed at a portion where the dehumidifier 301 and the accommodation room 101 communicate with each other, that is, on one side wall of the accommodation room 101.

The second pipe 380 is provided in a form connecting the second inlet 311 and the second outlet 321, so that air introduced through the second inlet 311 moves along the second pipe 380 and is dehumidified, and then discharged through the second outlet 321. Inside the second pipe 380, the second fan 330, the filtering member 340, and the evaporator and condenser (or thermoelectric module) of the heat pump 350, which are described above, may be provided. Accordingly, dehumidification may be performed while air moves inside the second pipe 380, and the dehumidified air may be supplied back to the accommodation room 101.

Although the drawing illustrates that the second inlet 311 is positioned below the second outlet 321, the second inlet 311 may be positioned above the second outlet 321.

The second outlet 321 is formed on one side wall of the accommodation room 101, so that the dehumidified air passed through the second outlet 321 may be supplied to the outside of the holder 400, thereby dehumidifying an outer surface of an object mounted on the holder 400. That is, when the object is a shoe, an outer skin of the shoe may be effectively dehumidified. Also, the dehumidified air supplied to the outside of the holder 400 may move to the inside of the object mounted on the holder 400 to dehumidify the inside of the object.

Figure 7:
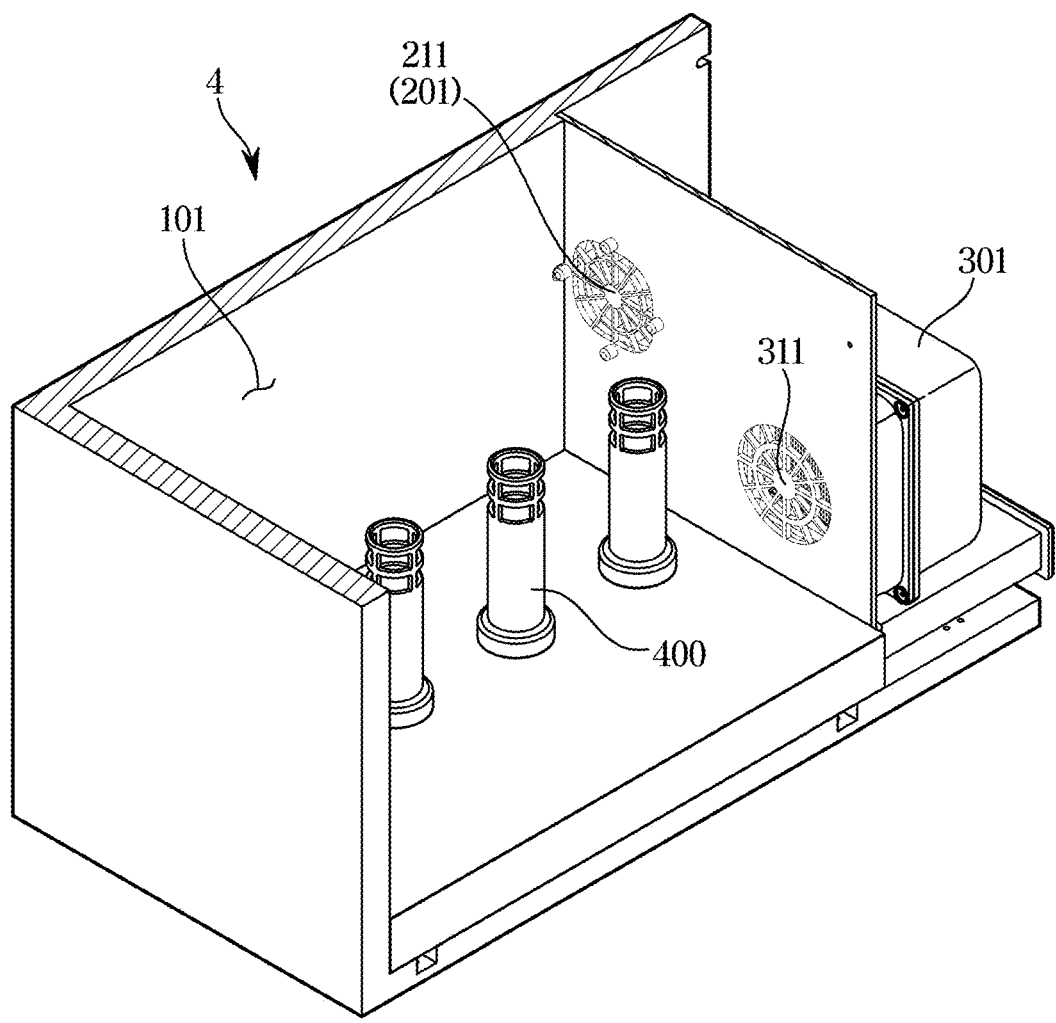
FIG. 7 illustrates a schematic view of a deodorization and dehumidification device according to another embodiment of the disclosure.
Figure 8:
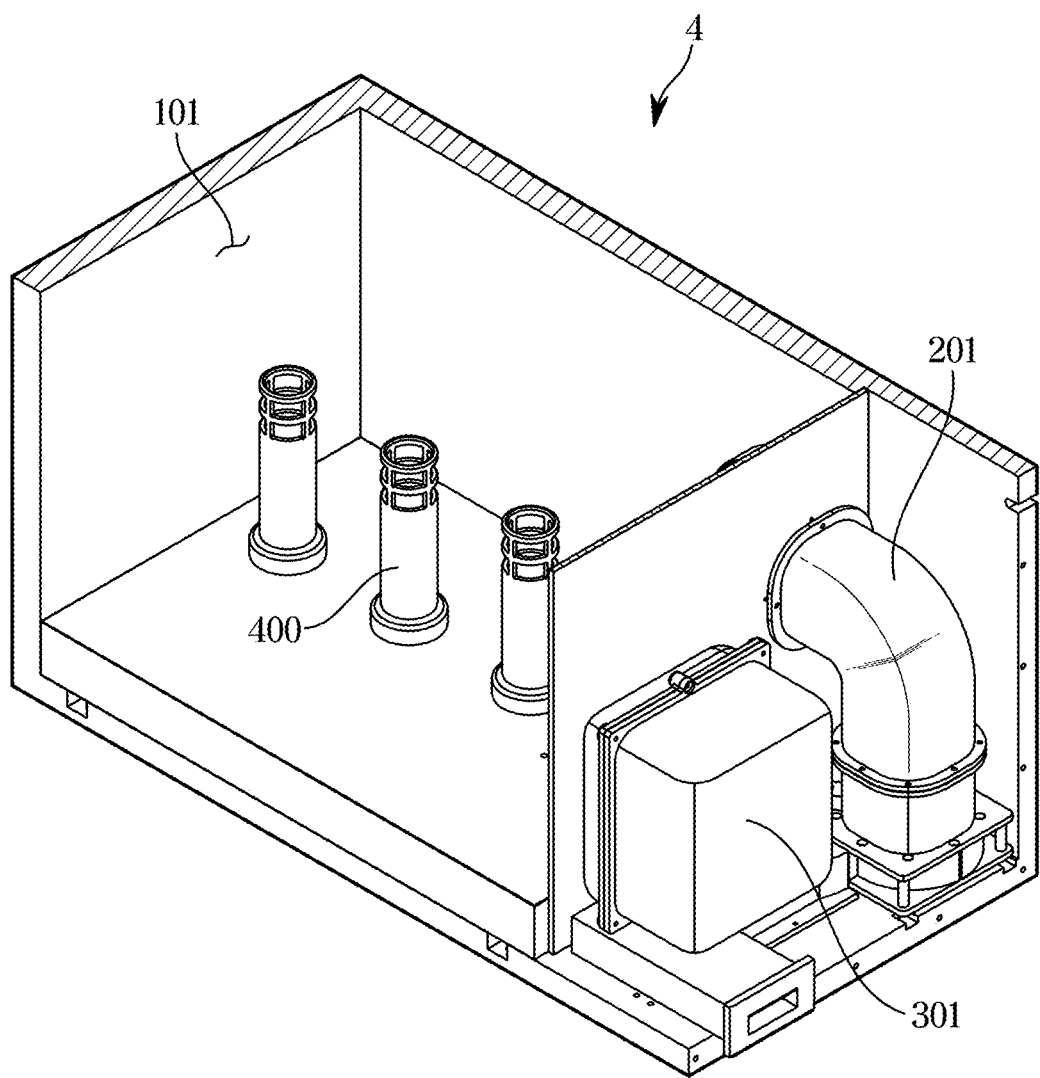
FIG. 8 illustrates a perspective view of the deodorization and dehumidification device in FIG. 7, viewed from a different angle.
Figure 9:
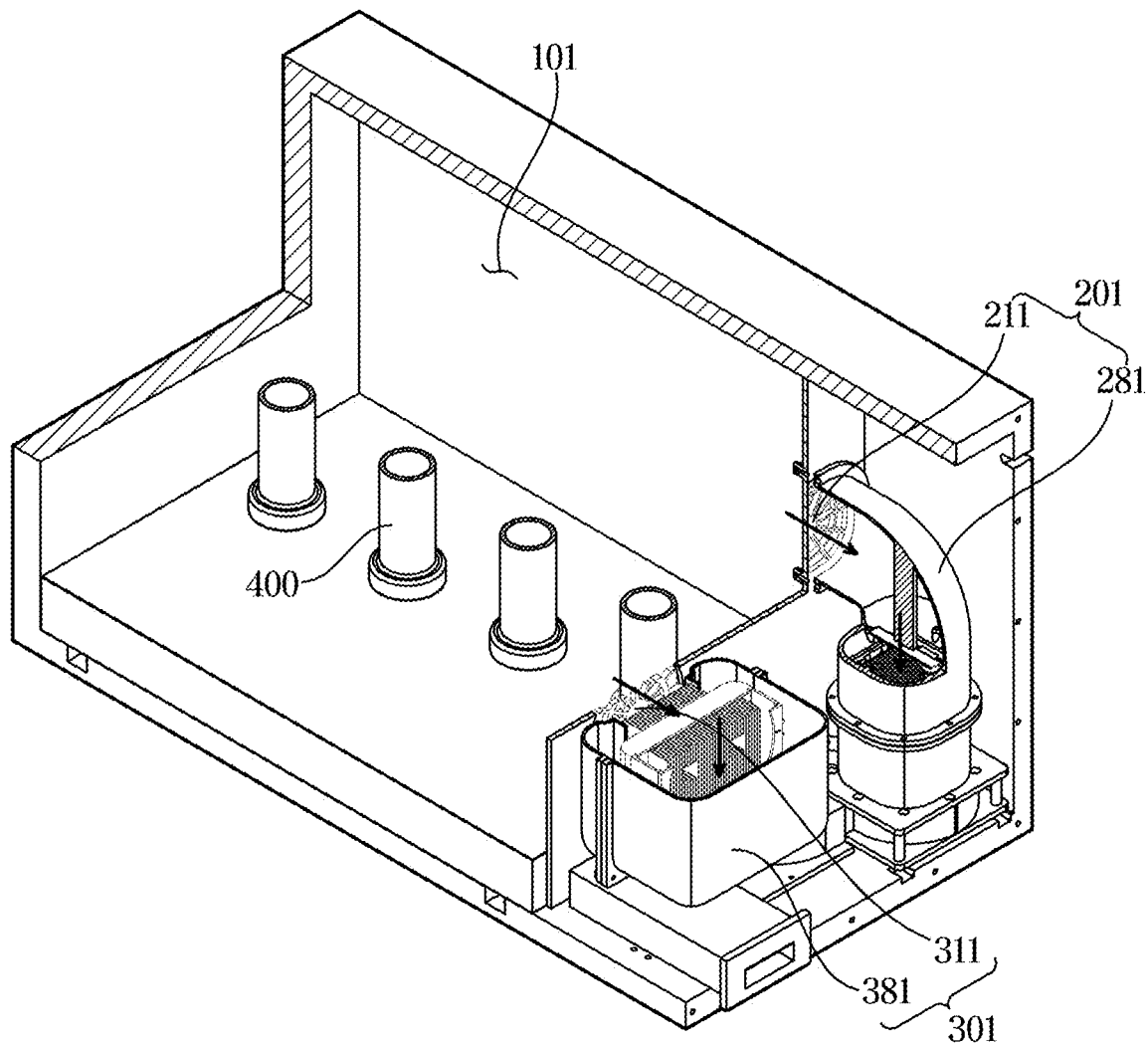
FIGS. 9 and 10 illustrate that air is introduced into a deodorizer and a dehumidifier through a first inlet and a second inlet, respectively, in the deodorization and dehumidification device in FIG. 7.
Figure 10:
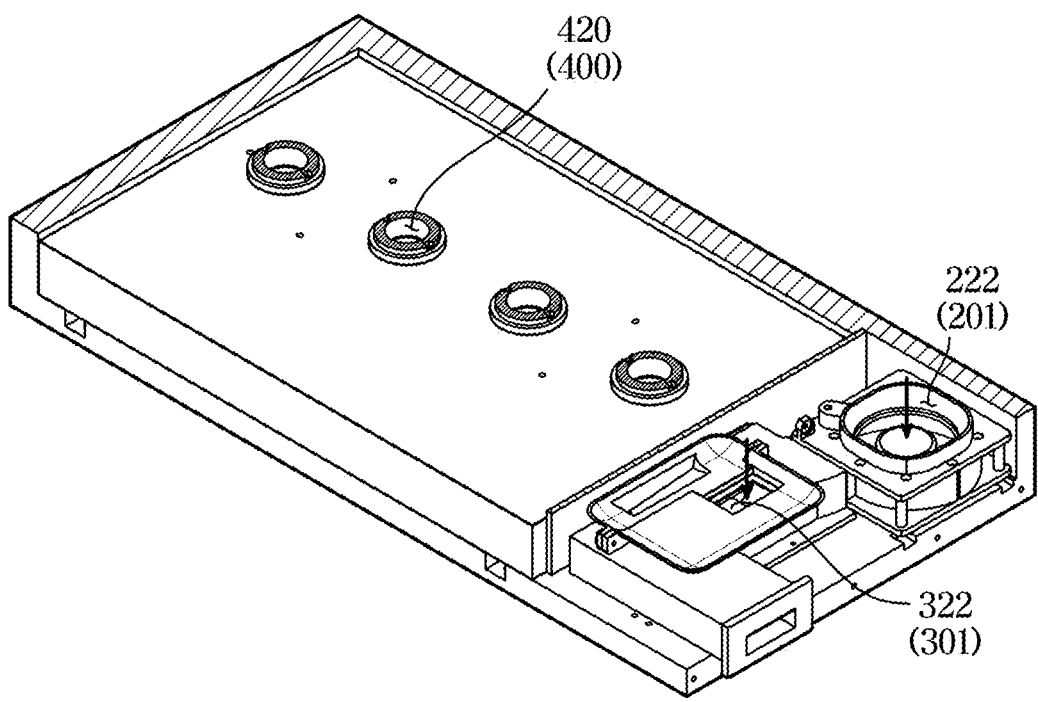
Figure 11:
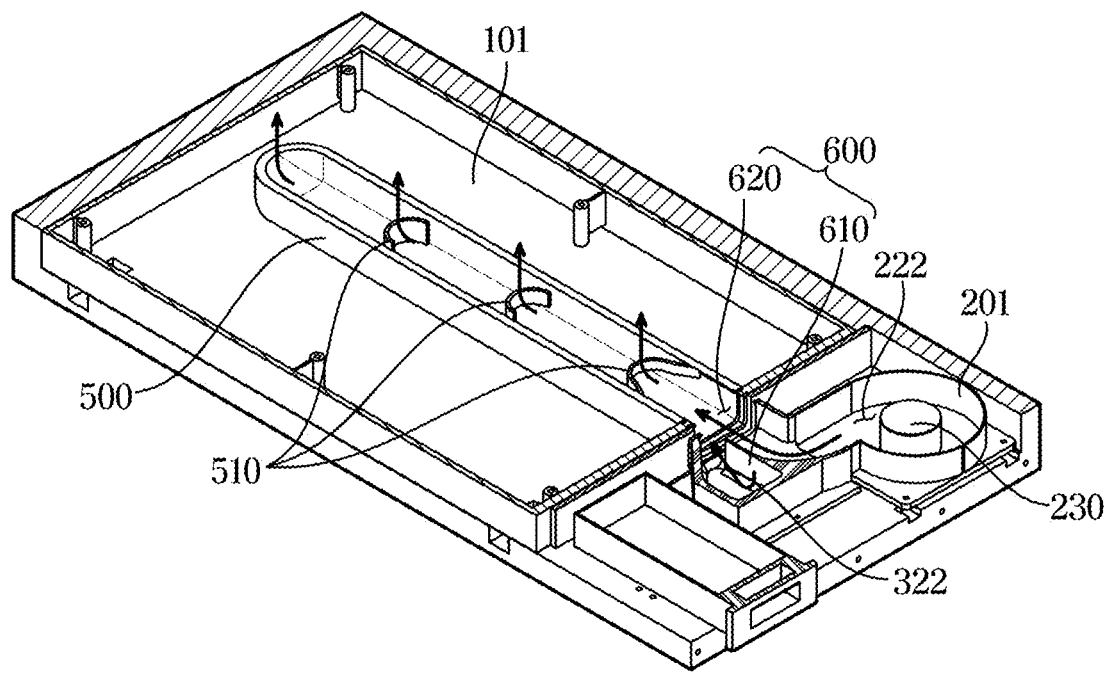
FIG. 11 illustrates that mixed air is introduced into a flow pipe in the deodorization and dehumidification device in FIG. 7.

FIG. 7 is a schematic view of a deodorization and dehumidification device according to another embodiment of the disclosure, FIG. 8 is a perspective view of the deodorization and dehumidification device in FIG. 7, viewed from a different angle, FIGS. 9 and 10 illustrate that air is introduced into a deodorizer and a dehumidifier through a first inlet and a second inlet, respectively, in the deodorization and dehumidification device in FIG. 7, and FIG. 11 illustrates that mixed air is introduced into a flow pipe in the deodorization and dehumidification device in FIG. 7.

Referring to FIGS. 7 to 11, a deodorization and dehumidification device 4 includes the accommodation room 101 in which an object is accommodated, the deodorizer 201 formed outside the accommodation room 101 to deodorize air in the accommodation room 101, the dehumidifier 301 formed outside the accommodation room 101 to dehumidify air in the accommodation room 101, and a mixing guide member 600 configured to supply air passed through each of the deodorizer 201 and the dehumidifier 301 to the inside of the accommodation room 101.

The deodorizer 201 includes the first inlet 211 communicating with the accommodation room 101 and a first pipe 281 extending from the first inlet 211, and the dehumidifier 301 includes the second inlet 311 communicating with the accommodation room 101 and a second pipe 381 extending from the second inlet 311. Accordingly, one part of air in the accommodation room 101 is introduced into the first pipe 281 through the first inlet 211 and deodorized in the first pipe 281, and the other part of air in the accommodation room 101 is introduced into the second pipe 381 through the second inlet 311 and dehumidified in the second pipe 381.

The first pipe 281 extends downward from the first inlet 211, and the second pipe 381 extends downward from the second inlet 311. As illustrated in FIG. 10, first and second outlets 222 and 322 are provided at lower ends of the first and second pipes 281 and 381, respectively.

Air introduced into the first pipe 281 and deodorized passes through the first outlet 222 and is supplied to the mixing guide member 600 connected to a lower end portion of the deodorizer 201, and air introduced into the second pipe 381 and deodorized passes through the second outlet 322 and is supplied to the mixing guide member 600 connected to a lower end portion of the dehumidifier 301.

The mixing guide member 600 is configured to be connected to the deodorizer 201 and the dehumidifier 301. That is, as illustrated in FIG. 11, the mixing guide member 600 may be formed at a lower portion of the dehumidifier 301 to be connected to the lower end portion of the deodorizer 201 in which the first fan 230 is provided, and at the same time to be connected to the lower end portion of the dehumidifier 301. Also, the mixing guide member 600 has a separating member 610 therein so that the air passed through the deodorizer 201 and the air passed through the dehumidifier 301 are not mixed and may be introduced into the accommodation room 101, respectively.

The mixing guide member 600 may include an outlet 620 communicating with the accommodation room 101 to allow air to be supplied to the accommodation room 101. Accordingly, the air passed through the deodorizer 201 and the air passed through the dehumidifier 301 may be supplied to the accommodation room 101 through the outlet 620 to be mixed in the flow pipe 500.

That is, the mixing guide member 600 serves to guide the air passed through the deodorizer 201 and the air passed through the dehumidifier 301 to be mixed in the flow pipe 500. However, although not shown, by the removal of the separating member 610, the mixing guide member 600 may allow the air passed through the deodorizer 201 and the air passed through the dehumidifier 301 to be mixed within the mixing guide member 600 and then to be supplied to the flow pipe 500.

As described above, the deodorized air and the dehumidified air are mixed with each other in the flow pipe 500 and are directly supplied to an object through the holder 400, so that deodorization and dehumidification of the object may be performed more effectively, and in particular, when the holder 400 is inserted into the object, the mixed air may be supplied to the inside of the object, so that deodorization and dehumidification may be efficiently performed inside the object.

Figure 12:
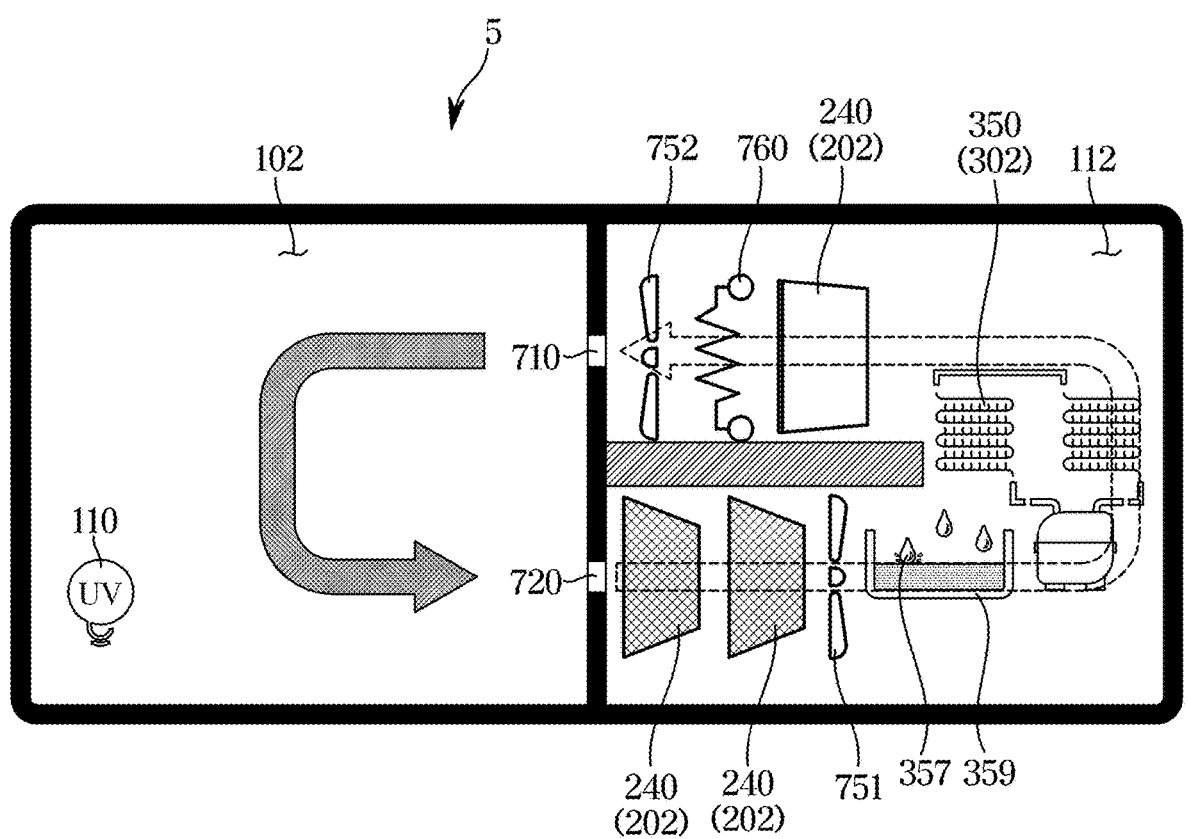
FIG. 12 illustrates a schematic view of a deodorization and dehumidification device according to another embodiment of the disclosure.

FIG. 12 is a schematic view of a deodorization and dehumidification device according to another embodiment of the disclosure.

A deodorization and dehumidification device 5 includes an accommodation room 102, a machine room space 112, a deodorizer 202, and a dehumidifier 302.

The accommodation room 102 is provided with an accommodation space in which an object is accommodated. The accommodation room 102 is formed such that at least one side thereof is open, so that an object may be accommodated therein. The ultraviolet irradiator 110 is installed inside the accommodation room 102 to sterilize an object by irradiating ultraviolet rays to the object.

The machine room space 112 is formed outside the accommodation room 102, and the deodorizer 202 and the dehumidifier 302 are located inside the machine room space 112.

The machine room space 112 includes a first hole 710 and a second hole 720 communicating with the accommodation room 102, the deodorizer 202 is located adjacent to the first hole 710, and the dehumidifier 302 is located adjacent to the second hole 720.

As indicated by an arrow in FIG. 12, air in the accommodation room 102 is introduced into the machine room space 112 through the first hole 710, passes through the deodorizer 202 to be deodorized, and then passes through the dehumidifier 302 to be dehumidified. The air deodorized and dehumidified as above passes through the second hole 720 and is supplied back to the accommodation room 102, so that deodorization and dehumidification of an object located in the accommodation room 102 may be performed.

That is, air in the accommodation room 102 passes through the deodorizer 202 and the dehumidifier 302 in sequence in the machine room space 112 outside the accommodation room 102 to be deodorized and dehumidified, and then is supplied back to the accommodation room 102.

In other words, air circulates through the accommodation room 102 and the machine room space 112 through one flow path, thereby deodorizing and dehumidifying an object located inside the accommodation room 102.

The deodorizer 202 may include the filter member 240, and the dehumidifier 302 may include the heat pump 350. Because the filter member 240 and the heat pump 350 have been described above, a description thereof will be omitted.

A first blade 751 and a second blade 752 may be provided inside the machine room space 112 to flow air in one direction through rotation so that the air continues to circulate. Also, a heater 760 may be provided inside the machine room space 112 to additionally remove moisture in air by supplying heat to air passed through the dehumidifier 302.

As is apparent from the above, a deodorization and dehumidification device according to the disclosure can prevent odors from being discharged to the outside of the device.

Further, the deodorization and dehumidification device according to the disclosure can improve deodorization and dehumidification efficiencies by performing deodorization and dehumidification of an object through routes different from each other.

Although the present disclosure has been described with various embodiments, various changes and modifications may be suggested to one skilled in the art. It is intended that the present disclosure encompass such changes and modifications as fall within the scope of the appended claims.

What is claimed is:

1. A deodorization and dehumidification device comprising:
  an accommodation room in which an object is accommodated;
  a deodorizer including a deodorization route provided outside of the accommodation room, the deodorizer configured to deodorize air in the accommodation room and supply the deodorized air to the accommodation room, wherein the deodorizer includes:
    a first inlet communicating with the accommodation room and configured to allow air in the accommodation room to be introduced; and
    a first outlet communicating with the accommodation room and configured to allow the deodorized air to be supplied to the accommodation room;
  a dehumidifier including a dehumidification route provided outside of the accommodation room and separated from the deodorization route, the dehumidifier configured to dehumidify air in the accommodation room and supply the dehumidified air to the accommodation room;
  a flow pipe connected to the first outlet and extended in one direction inside the accommodation room and configured to guide movement of the deodorized air;
  a plurality of holders arranged to be spaced apart a predetermined distance in an extending direction of the flow pipe is provided and connected to the flow pipe and on which the object is mounted so that the deodorized air is supplied to the object; and
  guide members extending from a bottom portion of an internal surface of the flow pipe and arranged to increase in height toward a direction of the movement of the deodorized air, wherein each guide member is aligned with a holder.

2. The deodorization and dehumidification device according to claim 1, wherein the deodorizer further comprises:
  a first fan configured to suck air in the accommodation room through the first inlet; and
  a filter member configured to remove odor particles contained in the sucked air.

3. The deodorization and dehumidification device according to claim 2, wherein the filter member comprises at least one of an activated carbon filter configured to adsorb and remove the odor particles by including activated carbon or a photocatalytic filter configured to decompose and remove the odor particles by irradiating light to the odor particles.

4. The deodorization and dehumidification device according to claim 2, wherein the deodorizer further comprises a heater configured to remove moisture contained in the air passed through the filter member by supplying heat.

5. The deodorization and dehumidification device according to claim 1, wherein the dehumidifier comprises:
  a second inlet communicating with the accommodation room and configured to allow air in the accommodation room to be introduced; and
  a second outlet communicating with the accommodation room and configured to allow the dehumidified air to be supplied to the accommodation room.

6. The deodorization and dehumidification device according to claim 5, wherein the dehumidifier further comprises:
  a second fan configured to suck air in the accommodation room into an inside of the dehumidifier; and
  a filtering member configured to filter out foreign matter contained in the sucked air.

7. The deodorization and dehumidification device according to claim 6, further comprising a heat pump comprising a compressor, a condenser, an expansion valve, and an evaporator to dehumidify the air sucked into the inside of the dehumidifier.

8. The deodorization and dehumidification device according to claim 6, further comprising a thermoelectric module comprising a heat absorbing plate and a heat radiating plate to dehumidify the air sucked into the inside of the dehumidifier.

* * * * *